(12) United States Patent
Tatarkiewicz et al.

(10) Patent No.: US 10,416,060 B1
(45) Date of Patent: Sep. 17, 2019

(54) APPARATUS AND METHOD FOR THREE-DIMENSIONAL DYNAMIC IMAGE ANALYSIS FOR PARTICLE VOLUME DETERMINATION

(71) Applicant: HORIBA Instruments Incorporated, Irvine, CA (US)

(72) Inventors: Jan J. Tatarkiewicz, San Diego, CA (US); Miroslav Pejcinovic, Lake Forrest, CA (US)

(73) Assignee: HORIBA INSTRUMENTS INCORPORATED, Irvine, CA (US)

( * ) Notice: Subject to any disclaimer, the term of this patent is extended or adjusted under 35 U.S.C. 154(b) by 0 days.

(21) Appl. No.: 16/431,274

(22) Filed: Jun. 4, 2019

(51) Int. Cl.
*G01N 21/00* (2006.01)
*G01N 15/06* (2006.01)
*G01N 15/00* (2006.01)

(52) U.S. Cl.
CPC ......... *G01N 15/06* (2013.01); *G01N 2015/03* (2013.01); *G01N 2015/0693* (2013.01)

(58) Field of Classification Search
CPC .... G01J 3/02; G01J 3/513; G01J 3/51; G01N 15/1459; G01N 21/65
USPC ......................................................... 356/73
See application file for complete search history.

(56) References Cited

U.S. PATENT DOCUMENTS

| 4,338,024 A | 7/1982 | Bolz |
| 5,296,910 A | 3/1994 | Cole |
| 5,359,907 A | 11/1994 | Baker |
| 6,061,130 A | 5/2000 | Plate |
| 7,907,279 B2 | 3/2011 | Seifert |
| 8,681,215 B2 | 3/2014 | King |
| 9,808,200 B2 * | 11/2017 | Raleigh .............. A61B 1/00177 |
| 9,897,525 B2 | 2/2018 | Spriggs |
| 9,909,972 B2 | 3/2018 | Tatarkiewicz |
| 10,184,875 B2 | 1/2019 | Beil |
| 2018/0186067 A1 * | 7/2018 | Buller ................... B29C 64/135 |

OTHER PUBLICATIONS

"Particle Size Analysis—Image Analysis Methods" ISO 13322-2 (Nov. 1, 2006).
Chopin, Josh, Hamid, Laga, and Miklavcic, Stanley, "A new method for accurate, high-throughput volume estimation from three 2D projective images" International Journal of Food Properties 2017, vol. 20, No. 10, 2344-2357.

\* cited by examiner

*Primary Examiner* — Md M Rahman
(74) *Attorney, Agent, or Firm* — Manuel de la Cerra

(57) ABSTRACT

A system for calculating the volume of a plurality of particles is disclosed. The system includes three optical assemblies, each with a light source directing a beam of light of a wavelength along an optical axis at a specimen chamber, a filter positioned along the optical path after the chamber, and a sensor positioned along the optical path after the filter. The wavelength of each beam of light is different from the other wavelengths, and each optical axis is orthogonal to the other optical axes. A processor is connected to the sensors in each of the optical assemblies, and the processors perform the following steps: (a) capture an image from each of the three sensors; (b) based on the images, calibrate each sensor; (c) after calibration, capture an image from each of the three sensors; and (d) determine a volume of the plurality of particles, based on the images captured in step (c).

8 Claims, 12 Drawing Sheets

(Method 200)

(Method 300)

APPARATUS AND METHOD FOR THREE-DIMENSIONAL DYNAMIC IMAGE ANALYSIS FOR PARTICLE VOLUME DETERMINATION

1.0 TECHNICAL FIELD

The present invention relates to a system for calculating the volume of particles in liquid samples using a microscope equipped with digital video cameras/sensors.

2.0 RELATED APPLICATIONS

None

3.0 BACKGROUND

This disclosure relates to the imaging of particles with diameters smaller than a few millimeters down to a few microns in dry or liquid samples using a microscope equipped with a digital video camera. The method of detection is bright field microscopy (the direction of observation is perpendicular to the illuminated background surface). The instrument to perform such an analysis comprises a cell (translucent tunnel) with particles falling or flowing inside it. Those particles are illuminated by a defocused (flat) light source present in the background and a video recording of light passing between particles (obfuscation); see e.g. U.S. Pat. Nos. 4,338,024; 5,296,910; and 5,359,907, all of which are incorporated herein by reference.

Different sizes and shapes of particles can be visualized and analyzed by dark images of particle silhouettes on the bright background. Typically, such instruments use only one video camera, with sophisticated models having two cameras but with parallel or nearly parallel axes (observing particles from the same direction but with different enlargement or observing transmitted and scattered light); see e.g. U.S. Pat. Nos. 6,061,130; 7,907,279; 8,681,215; 9,897,525; and 10,184,875, all of which are incorporated herein by reference.

The limitations of computer bandwidth and processing power has prevented, until recently, practical designs of instruments with more cameras observing particles from different, perpendicular directions that would make for better characterization of particles' shapes and ultimately better estimate their volume, which is of interest for many research and production facilities. Modern cameras and networking technology allow for multi-camera recording with high resolution.

With several cameras employed, however, it is very difficult to align all optical systems so that these devices record images for exactly same points or volumes of a sample in space. Therefore, a system and method for calibrating a multi-sensor system is needed.

4.0 SUMMARY

A system for calculating the volume of a plurality of particles is disclosed. The system includes three optical assemblies, each with a light source directing a beam of light of a wavelength along an optical axis at a specimen chamber, a filter positioned along the optical path after the chamber, and a sensor positioned along the optical path after the filter. The wavelength of each beam of light is different than the other wavelengths, and each optical axis is orthogonal to the other optical axes. A processor is connected to the sensors in each of the optical assemblies, and the processor performs the following steps: (a) capture an image from each of the three sensors; (b) based on the images, calibrate each sensor; (c) after calibration, capture an image from each of the three sensors; and (d) determine a volume of the plurality of particles based on the images captured in step (c).

The light sources may be a red, green and blue laser.

The system may further include a three-dimension calibration prism, constructed to be placed as a removable item in the chamber, or placed in the system in lieu of the chamber. The prism includes a calibration fiducial plane that intersects each of the three optical axes, and, within the calibration fiducial plane, a plurality of calibration fiducials that are separated by known distances. Prior to step (a), the calibration prism is placed at the chamber position. The images captured in step (a) include the calibration fiducials. The calibration of step (b) is based on the known distances of the calibration fiducials, and may include determining a rotational, a translational and a size calibration factor. The calibration prism may be removed after the calibration of step (b).

The plurality of calibration fiducials may include a center fiducial that is in the geometric center of the calibration prism and three outer calibration fiducials arranged as follows: the distance D1 between each of the outer fiducials is equal, and the distance D2 between each of the outer fiducials to the center fiducial is equal. D1 may be the same as D2.

Step (d) may further include the following steps: d(1) create a two-dimensional matrix based on the projection made by the particles for each image; d(2) extrapolate each two-dimensional matrix into a three-dimensional matrix; d(3) rotate the two-dimensional matrices, as needed, to align each of the two-dimensional matrices to the same coordinate system; d(4) combine all three-dimensional matrices to form a three-dimensional volume matrix; and d(5) calculate a volume based on the sum of the three-dimensional volume matrix. This final step may further be based on the size calibration factor.

A method for aligning and calibrating a system with three orthogonal optical assemblies is also disclosed. Each assembly includes a light source directing a light beam at a specimen chamber along an optical axis and a sensor positioned along the optical path to capture images of the specimen chamber. The method comprises the following steps: inserting an calibration prism into the system, wherein the calibration prism comprises a calibration fiducial plane that intersects each of the three optical axis, and, within the calibration fiducial plane, a plurality of calibration fiducials that are separated by known distances; activating each of the light sources; obtaining an image from each of the sensors; detecting the calibration fiducials in each obtained image; for each sensor, calculating a rotational, a translational and a size calibration factor based on locations of the calibration fiducials in the sensor image; and removing the calibration prism from the system.

The method may further include steps to determine a volume from the three optical assemblies. The follow steps carried out after the calibration prims have been removed from the system include: capturing an image from each of the three sensors; applying the rotational calibration factor and size calibration factor to the images; determining a volume of the plurality of particles based on the captured images by the following steps: creating a two-dimensional matrix based on the projection made by the particles for each image; extrapolating each two-dimensional matrix into a three-dimensional matrix; rotating, as necessary, the two-dimensional matrices to align each of the two-dimensional matrices to the same coordinate system; combining all three-dimensional matrices to form a three-dimensional volume matrix; and calculating a volume based on the sum of the three-dimensional volume matrix.

Additional aspects, alternatives and variations as would be apparent to persons of skill in the art are also disclosed herein and are specifically contemplated as included as part of the invention. The invention is set forth only in the claims as allowed by the patent office in this or related applications, and the following summary descriptions of certain examples are not in any way to limit, define or otherwise establish the scope of legal protection.

5.0 BRIEF DESCRIPTION OF THE DRAWINGS

The invention can be better understood with reference to the following figures. The components within the figures are not necessarily to scale, emphasis instead being placed on clearly illustrating example aspects of the invention. In the figures, like reference numerals designate corresponding parts throughout the different views and/or embodiments. It will be understood that certain components and details may not appear in the figures to assist in more clearly describing the invention.

6.0 DETAILED DESCRIPTION

Figure 1:
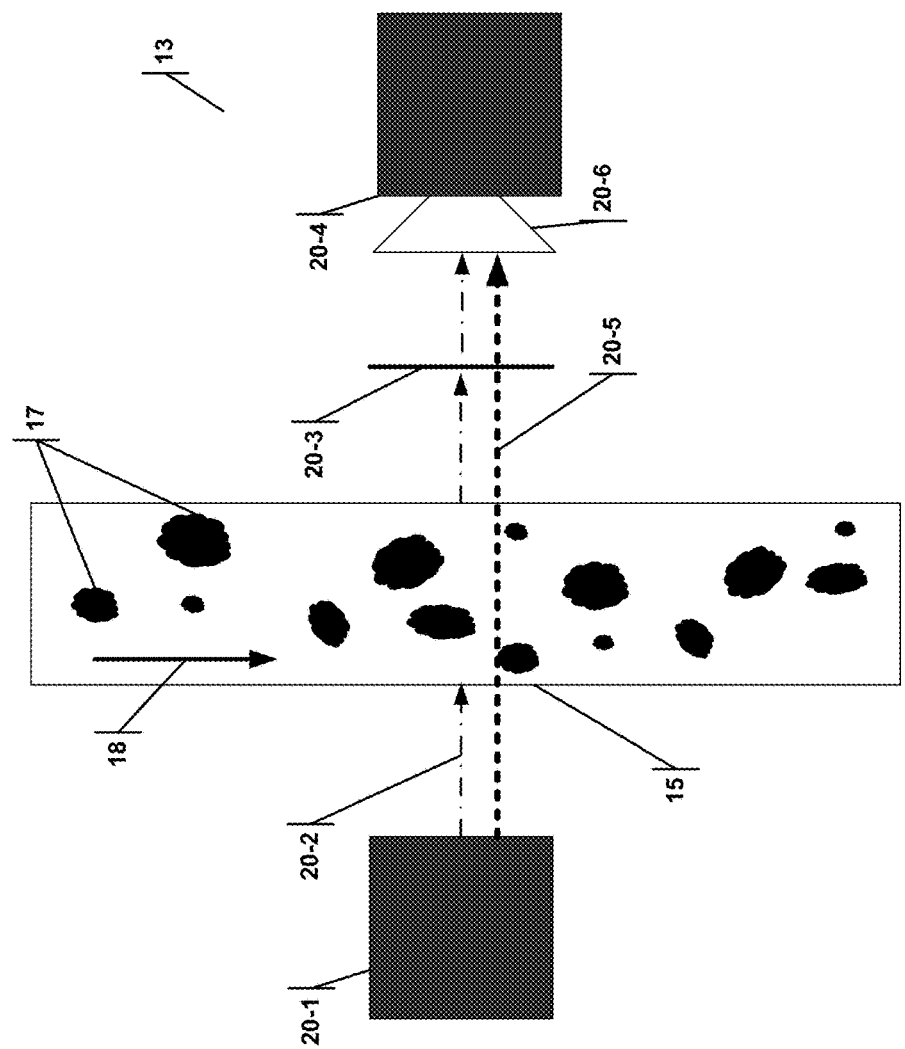
FIG. 1 illustrates a single optical assembly used in an apparatus for three-dimensional dynamic image analysis for particle volume determination.

Reference is made herein to some specific examples of the present invention, including any best modes contemplated by the inventor for carrying out the invention. Examples of these specific embodiments are illustrated in the accompanying figures. While the invention is described in conjunction with these specific embodiments, it will be understood that it is not intended to limit the invention to the described or illustrated embodiments. To the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, process operations well known to persons of skill in the art have not been described in detail in order not to obscure unnecessarily the present invention. Various techniques and mechanisms of the present invention will sometimes be described in singular form for clarity. However, it should be noted that some embodiments include multiple iterations of a technique or multiple mechanisms unless noted otherwise. Similarly, various steps of the methods shown and described herein are not necessarily performed in the order indicated, or performed at all in certain embodiments. Accordingly, some implementations of the methods discussed herein may include more or fewer steps than those shown or described. Further, the techniques and mechanisms of the present invention will sometimes describe a connection, relationship or communication between two or more entities. It should be noted that a connection or a relationship between entities does not necessarily mean a direct, unimpeded connection, as a variety of other entities or processes may reside or occur between any two entities. Consequently, an indicated connection does not necessarily mean a direct, unimpeded connection unless otherwise noted.

The following list of example features corresponds with the attached figures and is provided for ease of reference, where like reference numerals designate corresponding features throughout the specification and figures:

System 10
Optical Assembly 13
Transparent Chamber 15
Particles 17
Movement of Particles 18
1st Light Source 20-1
1st Wavelength 20-2
1st Filter 20-3
1st Sensor 20-4
1st Optical Axis 20-5
$1^{st}$ Optical Objective 20-6
2nd Light Source 30-1
2nd Wavelength 30-2
2nd Filter 30-3
2nd Sensor 30-4
2nd Optical Axis 30-5
$2^{nd}$ Optical Objective 30-6
3rd Light Source 40-1
3rd Wavelength 40-2
3rd Filter 40-3
3rd Sensor 40-4
3rd Optical Axis 40-5
$3^{rd}$ Optical Objective 40-6
Multi-Wavelength Light 50
Processor 50
3-D Calibration Prism 55
Calibration Fiducial Plane 60
Center Calibration Fiducial 65-1
Outer Calibration Fiducials 65-2
Distance between Outer Calibration Fiducials (D1) 70
Distance between Center and Outer Calibration Fiducials (D2) 75
Projection of Particle in a Single Plane 80

2D Pixel Matrix Representing the Projection of Particle 90-1, 90-2, 90-3
  Extrapolated 2D Matrix 92
  Rotated Extrapolated 2D Matrix 92-1
  Final Extrapolated 2D Matrix 93
  3D Matrices Created From Projections 95-1, 95-2, 95-3
  Combined Matrix Representative of Particle Volume (3D Volume Matrix) 100
    Image From Sensor 105
    Rotational Calibration Factor 110
    Image From Sensor Rotationally Calibrated 115
    Image From Sensor Rotationally and Translationally Calibrated 116
    Comparison Image Corresponding to Known Distances Between Calibration Fiducials 120
      Translational Calibration Factor 125
      Length Used for Size Calibration Factor 126
      Method for Calibrating And Aligning Three Optical Assemblies 200
      Method for Determining A Volume from the Three Optical Assemblies 300

This disclosure teaches how to select the same region of interest on all sensors, thus allowing for recorded images coming from exactly the same volume of illuminated channel in which particles are observed. Also disclosed is a method for reconstructing particle shapes by using their three perpendicular projections recorded by three perpendicularly placed sensors with different wavelengths light sources being used in opposing directions to each sensor, while each sensor has different wavelength filter(s) attached. Applying various wavelengths for illumination and detection separates obfuscated and scattered light recorded by each sensor to enhance the accuracy of the determination of particle projections and eventually leads to more accurate volume determination (more accurate outlines of silhouettes).

Specifically referring to FIG. 1, a single optical assembly 13 is shown, which is comprised of a first light source 20-1 that directs a beam of light 20-2 of a wavelength along an optical axis 20-5 at the specimen chamber 15. A filter 20-3 is positioned along the optical path 20-5 after the chamber 15, and the filter 20-3 preferentially allows the light 20-2 emitted from the first light source 20-1 through. A first sensor 20-4 is positioned along the optical path 20-5 after the filter 20-3, and may include an objective 20-6. Within the chamber are particles 17 that may move in the direction of arrow 18 either by freefall, a conveyer or flow as described in "Particle Size Analysis—Image Analysis Methods" ISO 13322-2 (2006-11-01), which is incorporated herein by reference.

Figure 2:
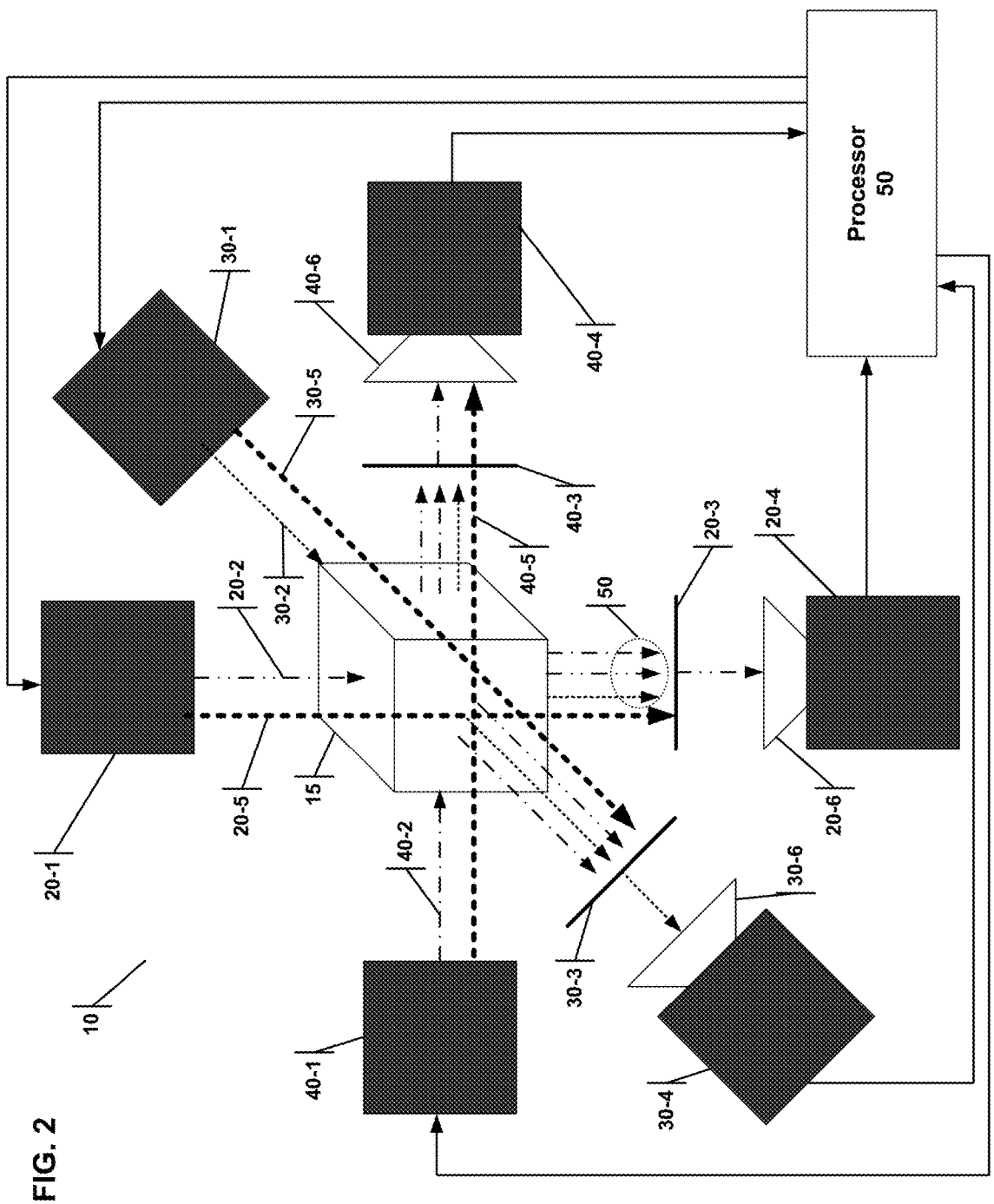
FIG. 2 illustrates three orthogonal optical assemblies used in an apparatus for three-dimensional dynamic image analysis for particle volume determination.

FIG. 2 illustrates a system 10 comprised of three optical assemblies of similar construction to the optical assembly 13 described with reference to FIG. 1. The additional optical assemblies therefore have a second and a third light source (30-1, 40-1) that each directs a beam of light (30-2, 40-2) along different axes paths (30-5, 40-5) at the specimen chamber 15. Each assembly also has a filter (30-3, 40-3) that preferentially allows the light (30-2, 40-2) emitted from the light source (30-1, 40-1) through. Moreover, each assembly has a sensor (30-4, 40-4) positioned along the optical path (30-5, 40-5) after the filter (30-3, 40-3).

To minimize light pollution from scattering, each optical assembly uses a light source (20-1, 30-1, 40-1) with a different wavelength (20-2, 30-2, 40-2). For example, a blue laser at about 450 nm, a green laser at about 520 nm and a red laser at 635 nm may be used. Each wavelength of light (20-2, 30-2, 40-2) is depicted in FIG. 2 with a unique line pattern. The filter (20-3, 30-3, 40-3) of a particular optical assembly is selected to preferential allow the wavelength of light associated with that optical assembly. Thus, when the filter 20-3 encounters multi-wavelength light 50, that filter 20-3 preferentially allows the light from light source 20-1 through. Each optical assembly may include an objective (20-6, 30-6, 40-6) connected to the sensor, enlarging the images between 1× and 10×. Each of the light sources (20-1, 30-1, 40-1) and sensors (20-4, 30-4, 40-4) is connected to the processor 50.

Modern digital video cameras have sensors with pixels that are about 5 microns by 5 microns in size and range from 640 pixels by 480 pixels for a standard VGA resolution up to about 2000 pixels by 2000 pixels for very high-resolution cameras. Thus, the observation field covered by each sensor may be between 10 mm by 10 mm for large sensors with small enlargement down to a fraction of that field for high-enlargement small sensors.

Because the system 10 uses three separate optical assemblies to image the specimen chamber, the sensors/images from the optical assemblies must be calibrated and aligned. This is especially true given that the particles that may be introduced into the specimen chamber may be on the order of microns.

Figure 3A:
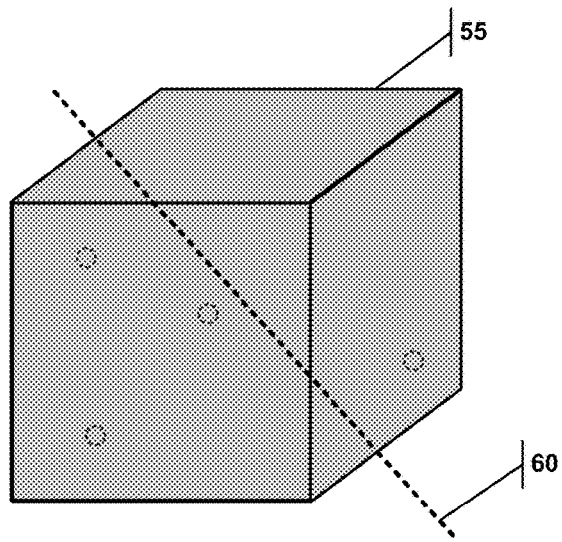
FIG. 3A illustrates a calibration prism.
Figure 3B:
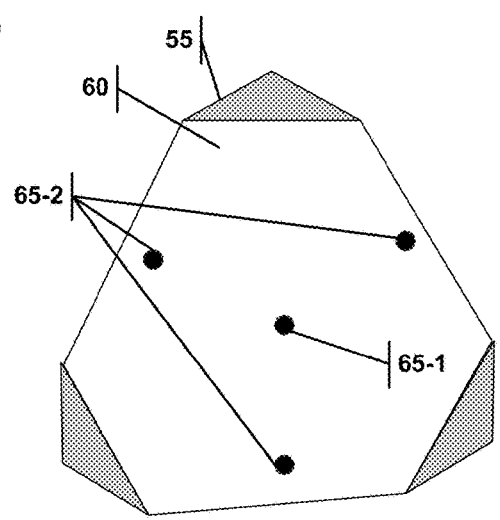
FIG. 3B illustrates the calibration prism cleaved along the calibration fiducial plane.
Figure 3C:
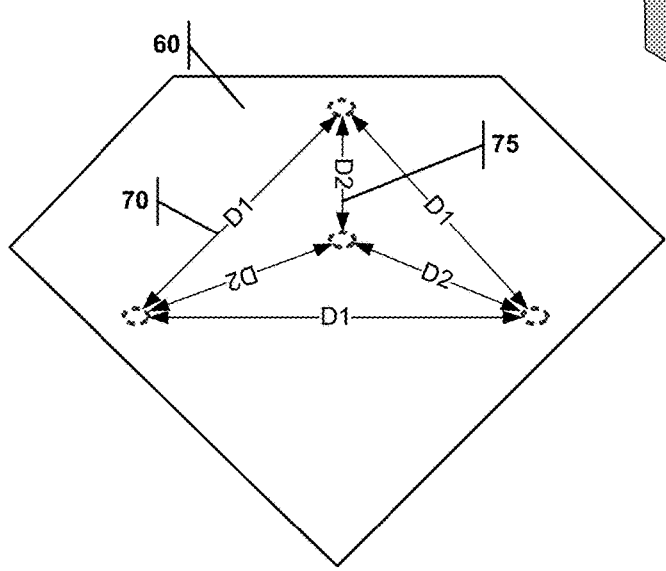
FIG. 3C illustrates the calibration fiducial plane with the calibration fiducial distances.

Due to mechanical inaccuracy of placing fairly large optical assemblies, FIGS. 3A-3C disclose a 3D calibration prism 55 at which each optical assembly can be pointed. FIG. 3A illustrates that the 3D calibration prism 55 is a cube with calibration fiducials within. FIG. 3B is the 3D calibration prism 55 cleaved along the line 60, which exposes a calibration fiducial plane 60 on which a center calibration fiducial 65-1 and outer calibration fiducials 65-2 are marked or etched. In a preferred embodiment, this plane is 54.73 degrees offset from each of the 3D calibration prism's faces, which in turn makes it offset from the plane of sensor, which is orthogonal to the optical axes. Thus, each of the three sensors can see all the calibration fiducials (65-1, 65-2). Moreover, to observe smaller than 1 mm and larger than 10 microns, the system 10 may use a long working-distance objectives with very low enlargement—possibly 2×. These objectives have a very large depth of field of many hundreds of microns; hence, the center calibration fiducial 65-1 and the outer calibration fiducials, although viewed at the angle, will be in focus, giving precise positioning and orientation of each sensor relative to the same object.

The center calibration fiducial 65-1 and outer calibration fiducials 65-2 are a known and precise distance D2 from each other, and the outer calibration fiducials 65-2 are a known and precise distance D1 from each other. Since these distances are known with a high accuracy (etched microscales are used to create this points), the number of pixels per optical assembly is individually calibrated, arriving at a number of pixels per unit of length. These distances D1 and D2 may be equal or different.

Figure 4:
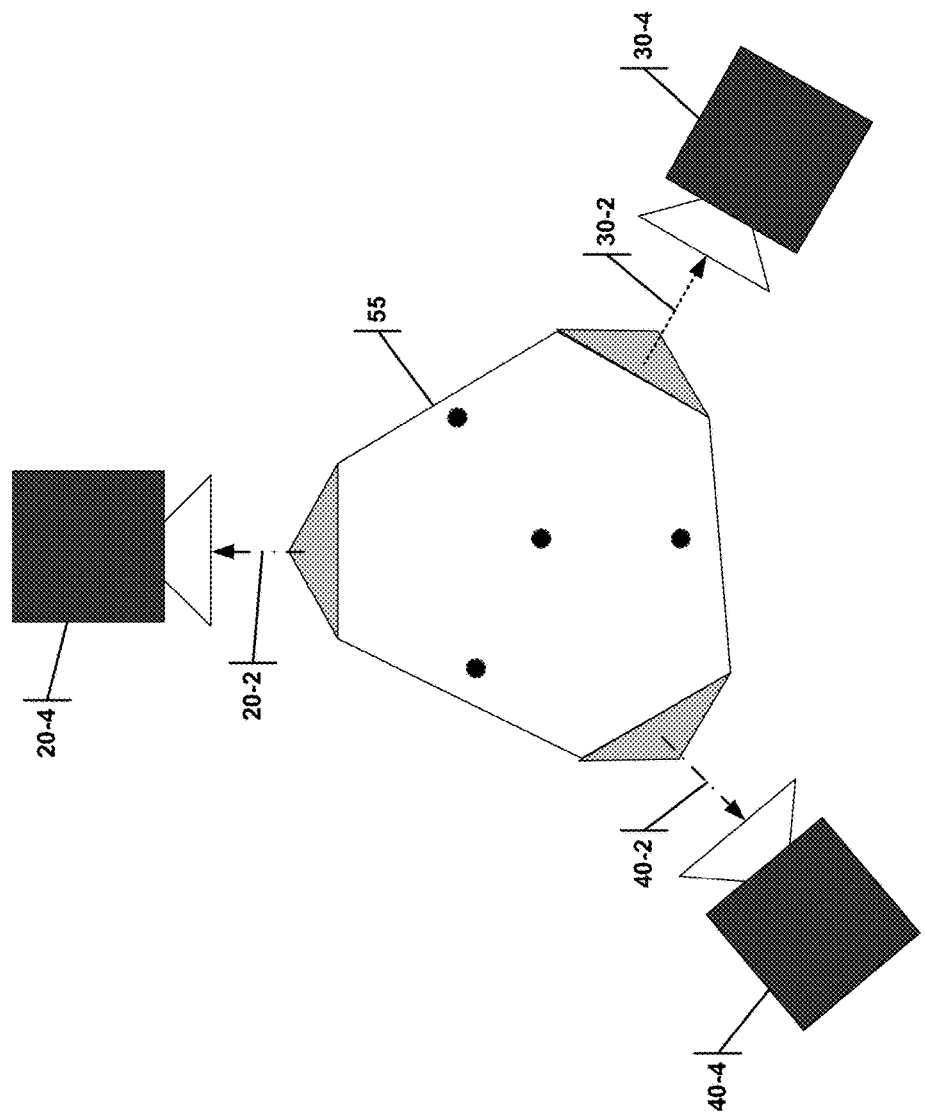
FIG. 4 illustrates the calibration prism used with the three sensors.

As depicted in FIG. 4, the 3D calibration prism 55 is placed in the specimen chamber 15. Alternatively, the specimen chamber 15 may be removed and the 3D calibration prism 55 inserted in its place. Each sensor (20-4, 30-4, 40-4) points to the 3D calibration prism 55. The sensors (20-4, 30-4, 40-4) may be mechanically adjusted as to center each sensor's (20-4, 30-4, 40-4) field of view on the center calibration fiducial 65-1. Also, electronic shifting of the region of interest (ROI) for each sensor (20-4, 30-4, 40-4) by the processor 50 can center.

Since all objectives are never exactly the same (i.e. they may have slightly different enlargement factors), the outer calibration fiducials 65-2 with known distances between them may be used to precisely calibrate each sensor-objective set. Additionally, the line created by each pair of outer calibration fiducials 65-2 allows for the precise orientation (rotation) of each sensor image. A technique for calibration is disclosed by one of the inventors of this application in U.S. Pat. No. 9,909,972, which is incorporated herein by reference.

Figure 5:
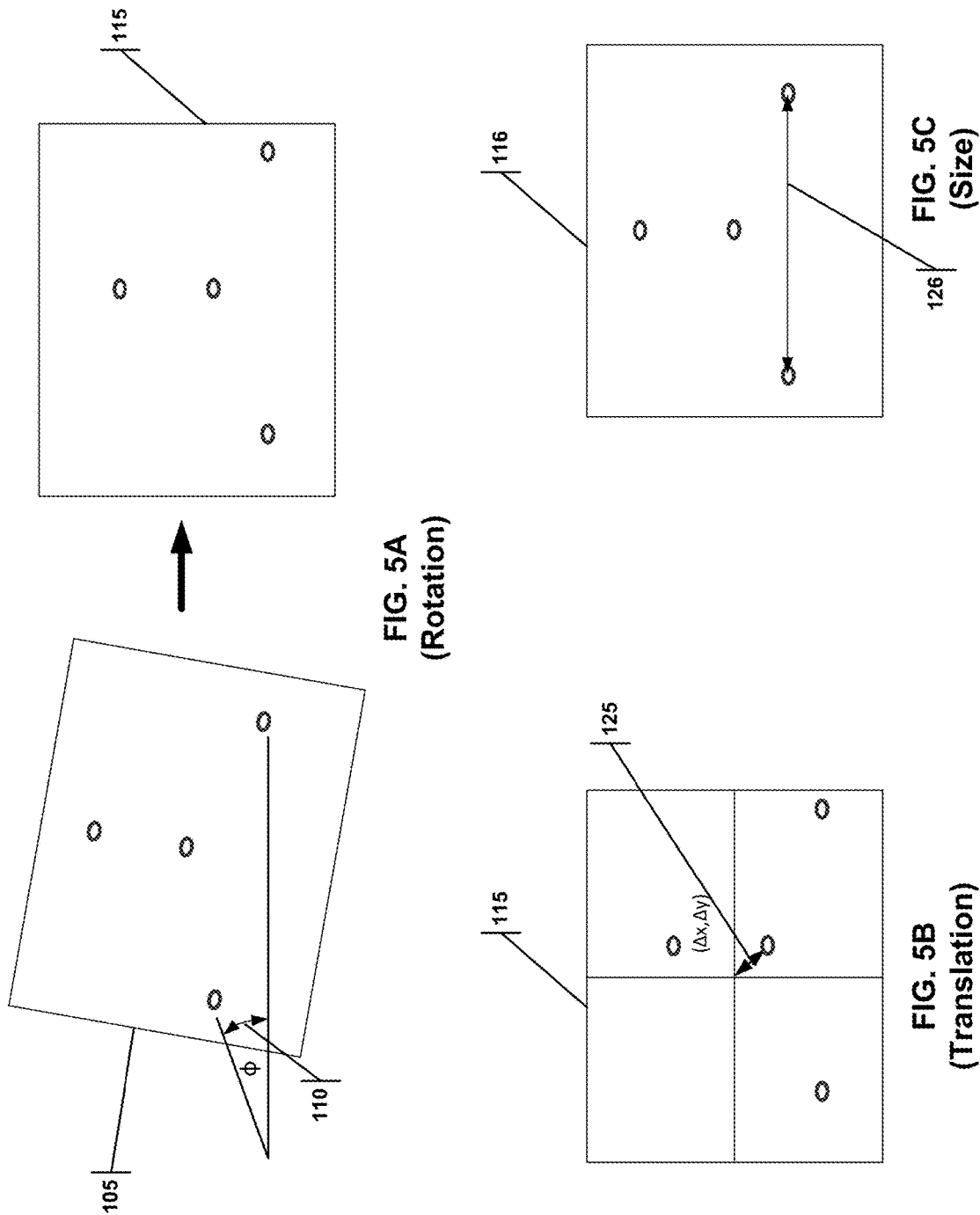
FIG. 5A illustrates the rotational calibration factor.
FIG. 5B illustrates the translational calibration factor.
FIG. 5C illustrates the size calibration factor.

There may be three calibration factors necessary for proper calibration and alignment for each optical assembly in the system: translational, rotational and size. FIG. 5A, 5B, 5C show a three-step process for proper alignment and calibration. In FIG. 5A, the lower two outer calibration fiducials are not horizontal, so the processor 50 can apply a rotational calibration factor $\phi$ 110 to correct this. While the horizontal was chosen in this example, it would be apparent that other reference lines may be used to arrive at the rotational calibration factor $\phi$ 110. The center of the rotated image 115 is then aligned with the center calibration fiducial 65-1, and a translational calibration factor $(\Delta x, \Delta y)$ 125 is determined. These two factors may be combined as follows:

$$x' = x \cos \phi + y \sin \phi + \Delta x \qquad \text{Equation (1)}$$

$$y' = -x \sin \phi + y \cos \phi + \Delta y \qquad \text{Equation (2)}$$

where (x, y) are the pixel numbers (coordinates) in two directions on raw image 105, and (x', y') are the coordinates for the rotationally and translationally calibrated image 116, with a translational calibration factor between the two images of $(\Delta x, \Delta y)$ 125 and a rotational calibration factor of angle $\phi$ 110.

In FIG. 5C, the distance between two fiducials is measured as a total number P of pixels 125. Since this distance L is known precisely, a size calibration factor can be determined by the ratio of L/P in units of [microns/pixel]. This size calibration factor is used when determining the volume of single pixel. Since each sensor will likely have a different L/P ratio, the volume of single pixel (i.e., a voxel) will be as follows:

$$\text{Voxel} = (L1/P1) \times (L2/P2) \times (L3/P3) \qquad \text{Equation (3)}$$

Where L1/P1 is the L/P ratio for the first sensor, L2/P2 is the L/P ratio for the second sensor, and L3/P3 is the L/P ratio for the third sensor.

These calibration factors are unique for each optical assembly, and the processor can apply these factors to images captured by the sensors prior to processing.

Figure 6:
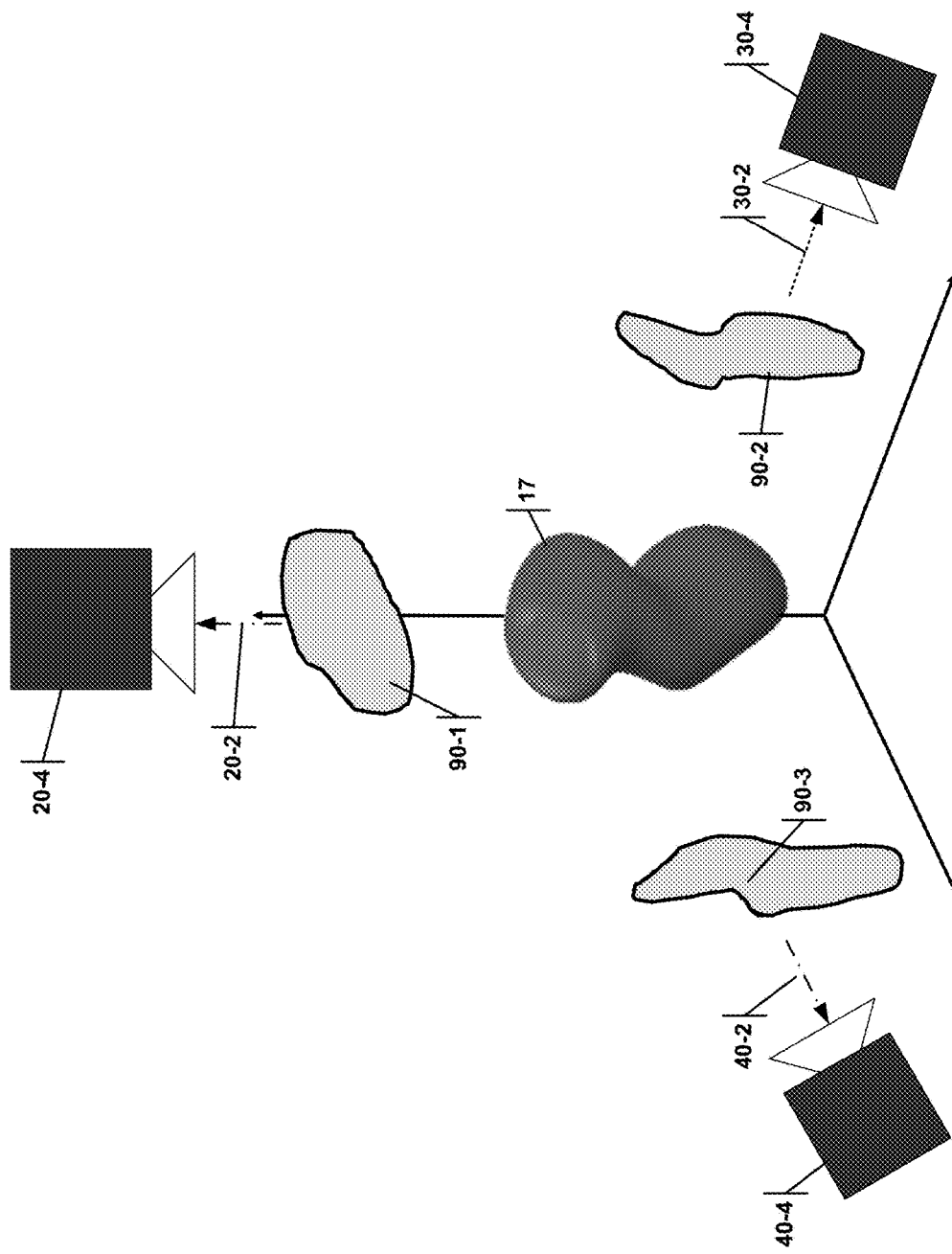
FIG. 6 depicts the projection of a particle in three different orthogonal planes with three sensors and three wavelengths.
Figure 7:
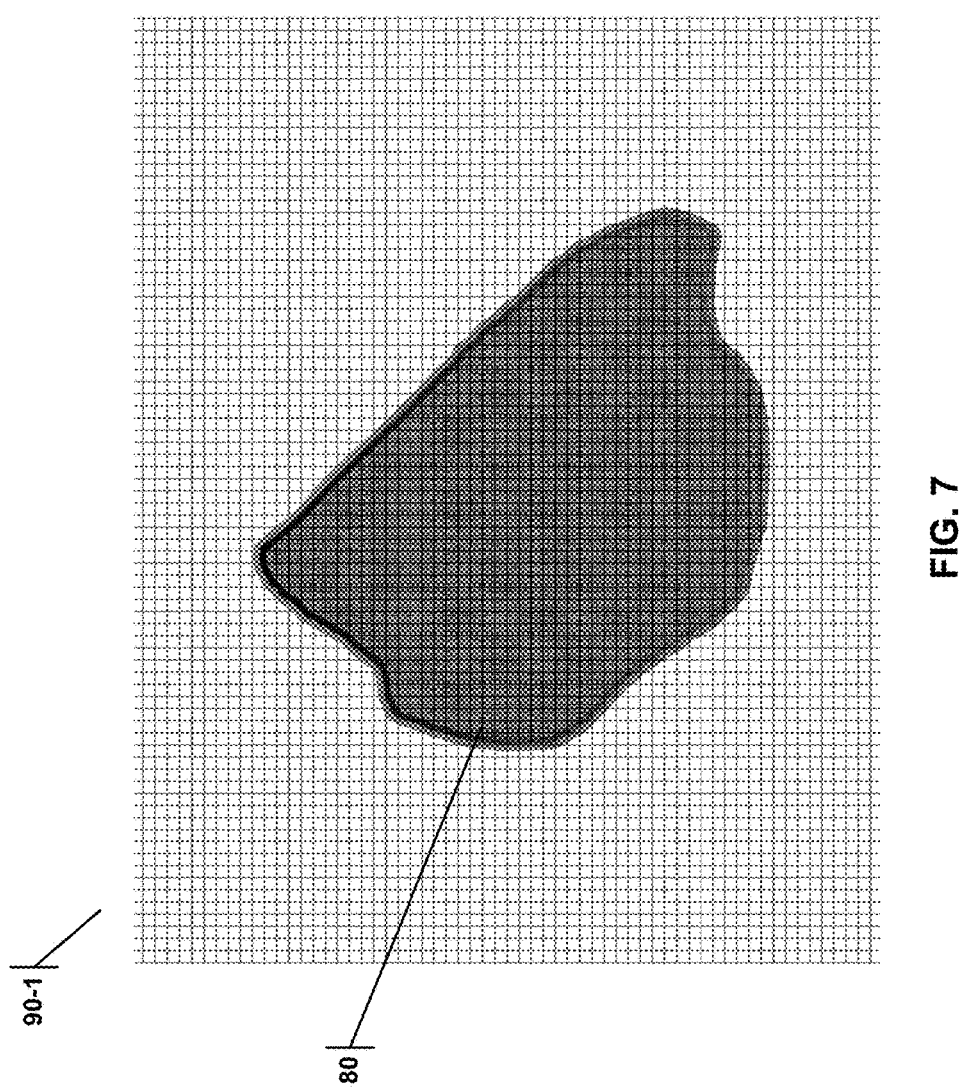
FIG. 7 illustrates the projection of a particle in a single plane, to create a two-dimensional matrix.
Figure 8:
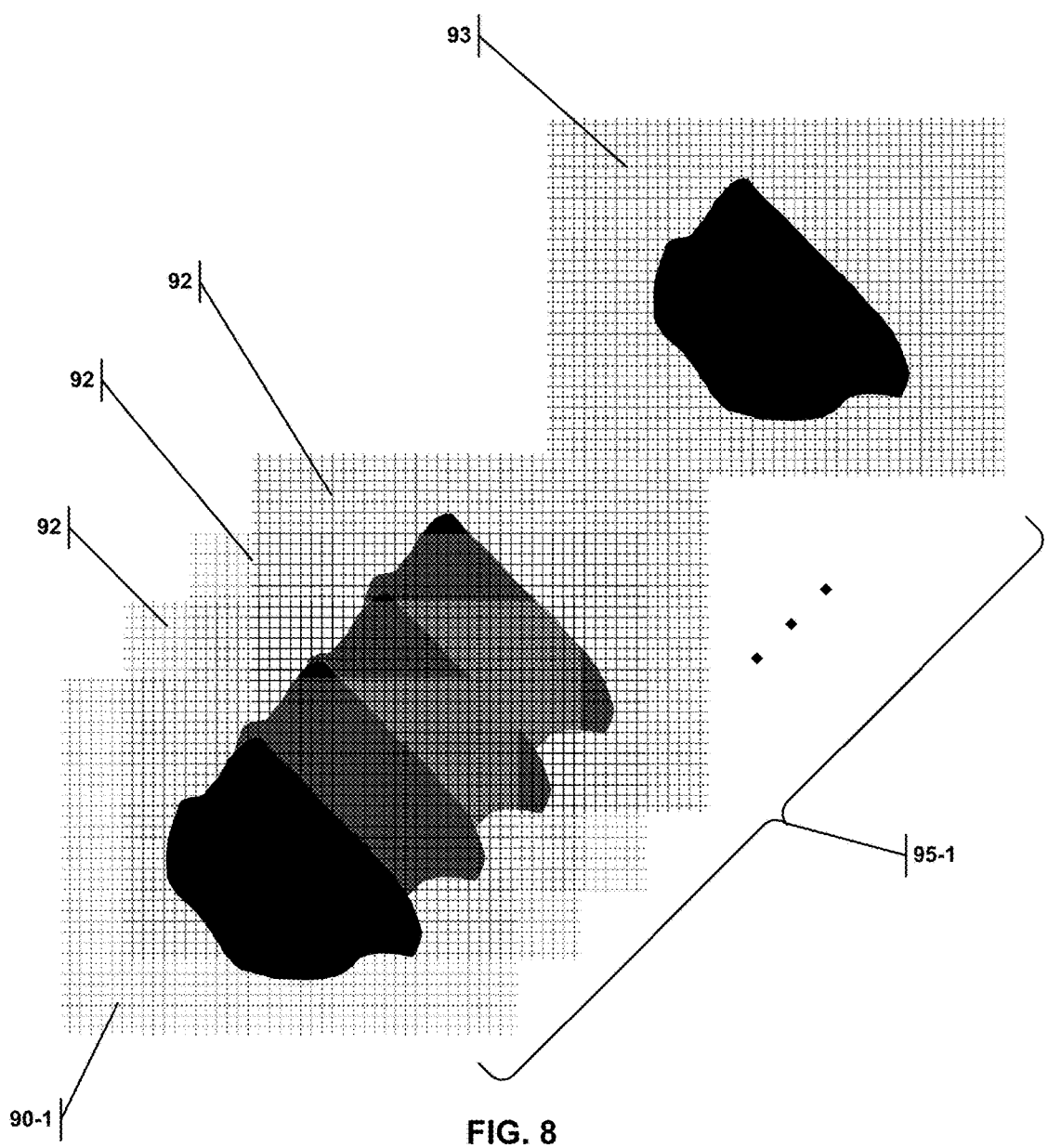
FIG. 8 illustrate how a three-dimensional matrix is created from the two-dimensional matrix.
Figure 9:
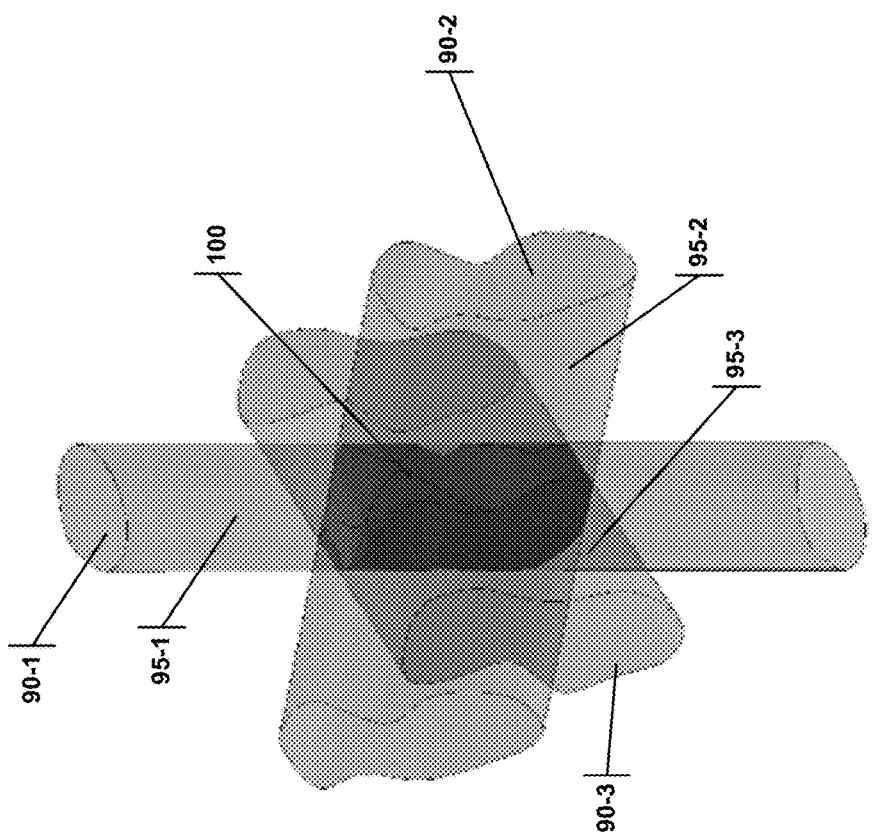
FIG. 9 is a graphical depiction of the three matrices created from the projections, to create a single matrix that is representative of the particle volume.

Due to the pixelated nature of images taken by digital video sensors, each particle's projection recorded by the sensor is confined or filled by a set of pixels that are dark (low light detection level or zero) as opposed to the pixels that do not contain silhouette of a particle (these are high intensity pixels or ones). Hence each projection can be represented as a two-dimensional matrix of 0s and is stored in processor memory. Since all three sensors should be synchronized aligned and calibrated, when a particle goes through the specimen chamber, the system will generate three pixelated images, each with a known space orientation and a known scale of distances. This is shown in FIG. 6, where a particle 17 casts a different projection on each sensor (20-1, 30-1, 40-41). This projection can be converted to a 2D pixel matrix 90-1 (FIG. 7), where pixels that experience the projection register a 1, and the others register a 0. The 2D matrix is then extrapolated 92 by repeating the conversion in the direction orthogonal to the plane of the image sensor, creating a 3D matrix 95-1 (see FIG. 8). This processes is repeated for each projection for all three sensors, yielding three 3D matrices (95-1, 95-2, 95-3), that, when combined, yield a combined matrix that is representative of the particle volume 100 (see FIG. 9).

Figure 10:
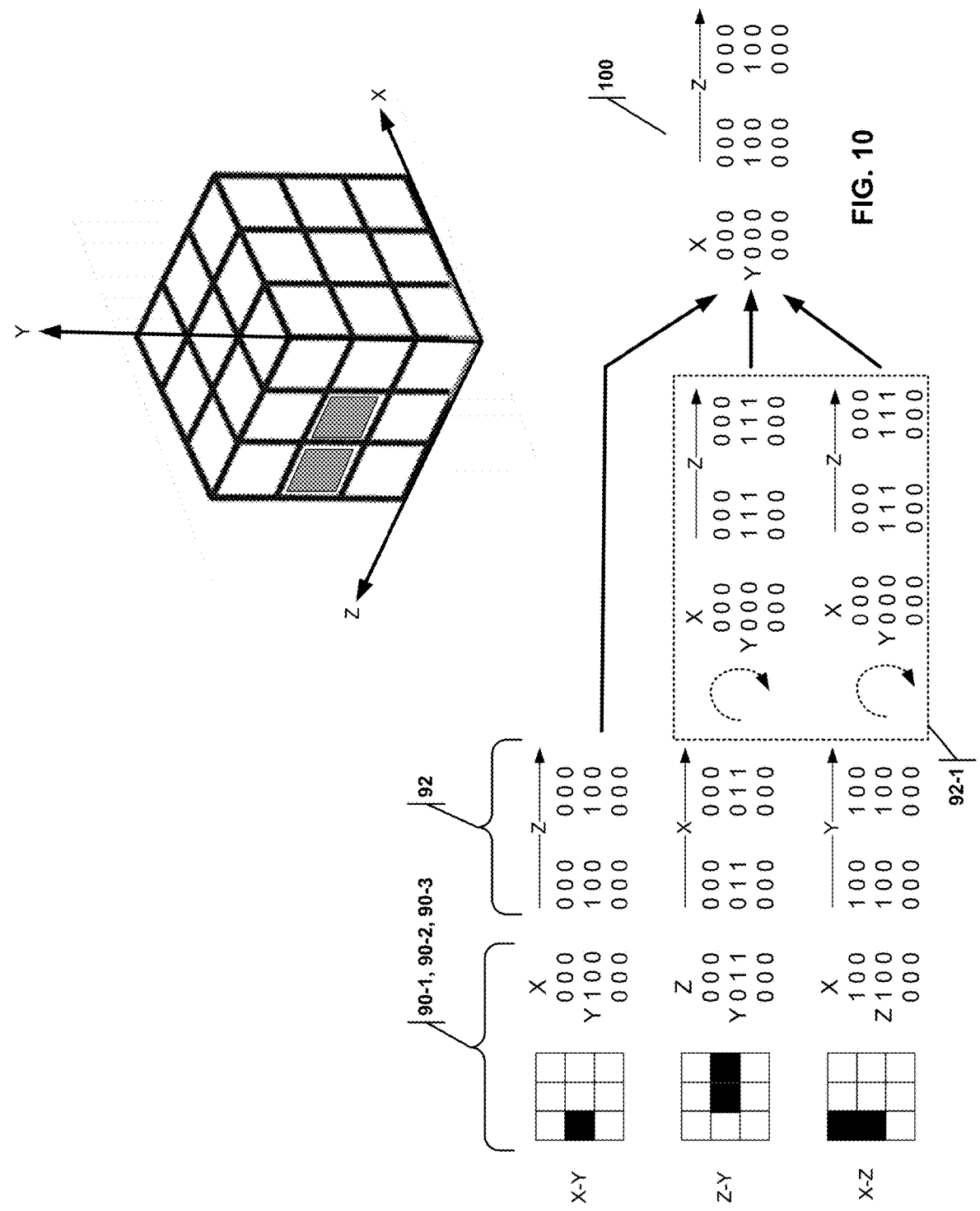
FIG. 10 illustrates the projections, the creation of matrices and the combination of those matrices for a 3×3×3 pixel volume.

This projection, formation of 2D matrices, extrapolation and combination is shown for a simple 3×3×3 volume in FIG. 10. The 3×3×3 cube represents pixel space, and the two gray sub-cubes represent where the particle is within the pixel space. The three projections and projection matrices (90-1, 90-2, 90-3) are shown and created by assigning a "1" in every spot on the 3×3 matrix where a projection is detected, and this is done for each of the three orthogonal planes. Those 2D matrices (90-1, 90-2, 90-3) are then extrapolated 92 by repeating the same 2D matrix into the plane orthogonal to the projection plane. The matrices for the Z-Y and X-Z sensor need to be rotated 92-1 before they are combined. The rotation orients each matrix to the same global X-Y-Z coordinate set. The combined matrix 100 is an AND logical operation of the three matrices, meaning that if a 1 is present in the same position for all three matrices then the combined matrix will also hold a 1; otherwise, the combined matrix will hold a 0 at that position. The resultant combined matrix 100 indicates that there is particle matter at two positions, which is what was expected. To determine the actual volume of the particle in this example, the combine matrix is summed by adding all the ones (1's), and that summation is multiplied by the voxel (Eq. 3).

By processing several hundred or even thousands of particles by the above described method, one can get good enough statistics to estimate the particle volume distribution of a given sample that is being run through the system. The proposed method for measuring particle volumes is known to overestimate the actual volume by less than 20%, depending on the shape of the particles being studied (simulation of various shapes): volumes of more symmetrical or regular particles are estimated much more accurately, while only those that have cavities or twisted shape will end up at the upper limit of overestimation.

Figure 11:
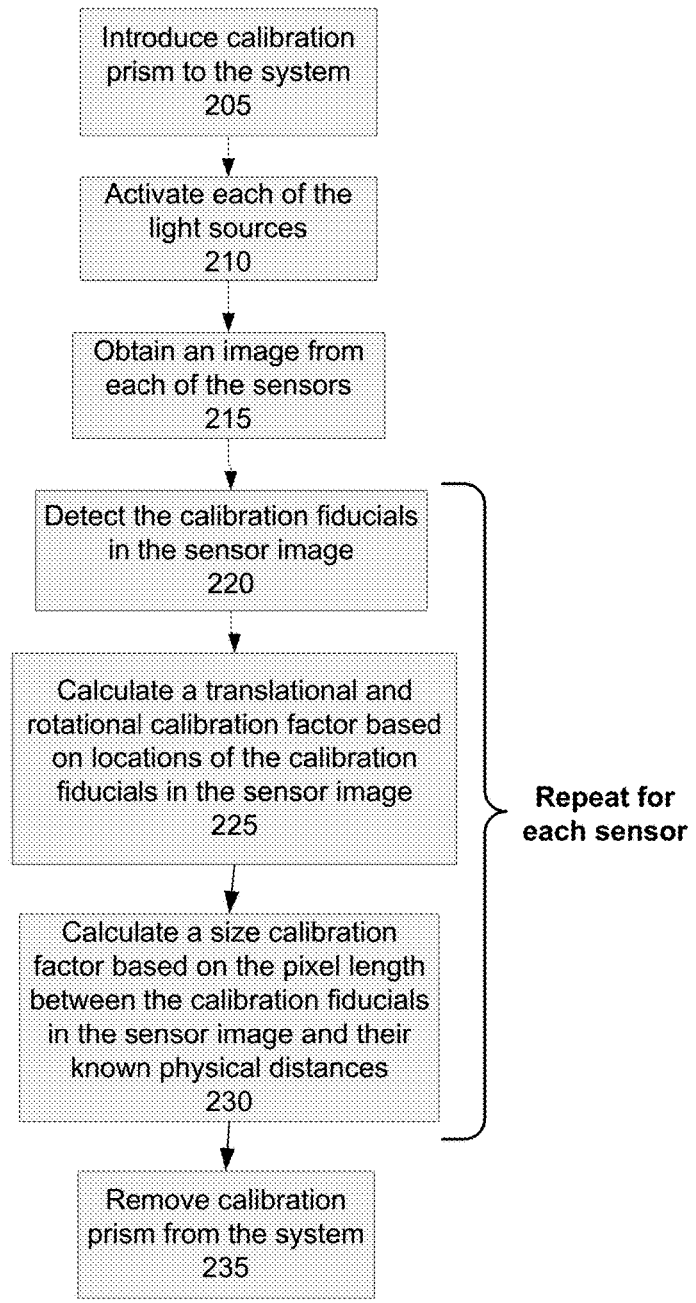
FIG. 11 is a flowchart for a method to align and to calibrate three orthogonal optical assemblies.

FIG. 11 is a flowchart of a method 200 to align and calibrate three orthogonal optical assemblies, such as the system described with reference to FIG. 2. A 3D calibration prism as described above is introduced into the system at step 205. This can be done by placing the 3D calibration prism 55 into the specimen chamber 15. Alternatively, the specimen chamber 15 may be removed and the 3D calibration prism 55 inserted in its place. The processor activates each of the light sources at steps 210 and obtains an image from each of the sensors at step 215. For each sensor, the calibration fiducials are detected (step 220) and the translational and rotational calibration factors are calculated in step 225, as described above. The size calibration factor is also calculated based on the pixel length between the calibration fiducials in the sensor image and their known physical distances, as described above (step 230). Steps 220, 225 and 230 are performed for each sensor, and the calibration factors are stored. Finally, the 3D calibration prism is removed from the system.

Figure 12:
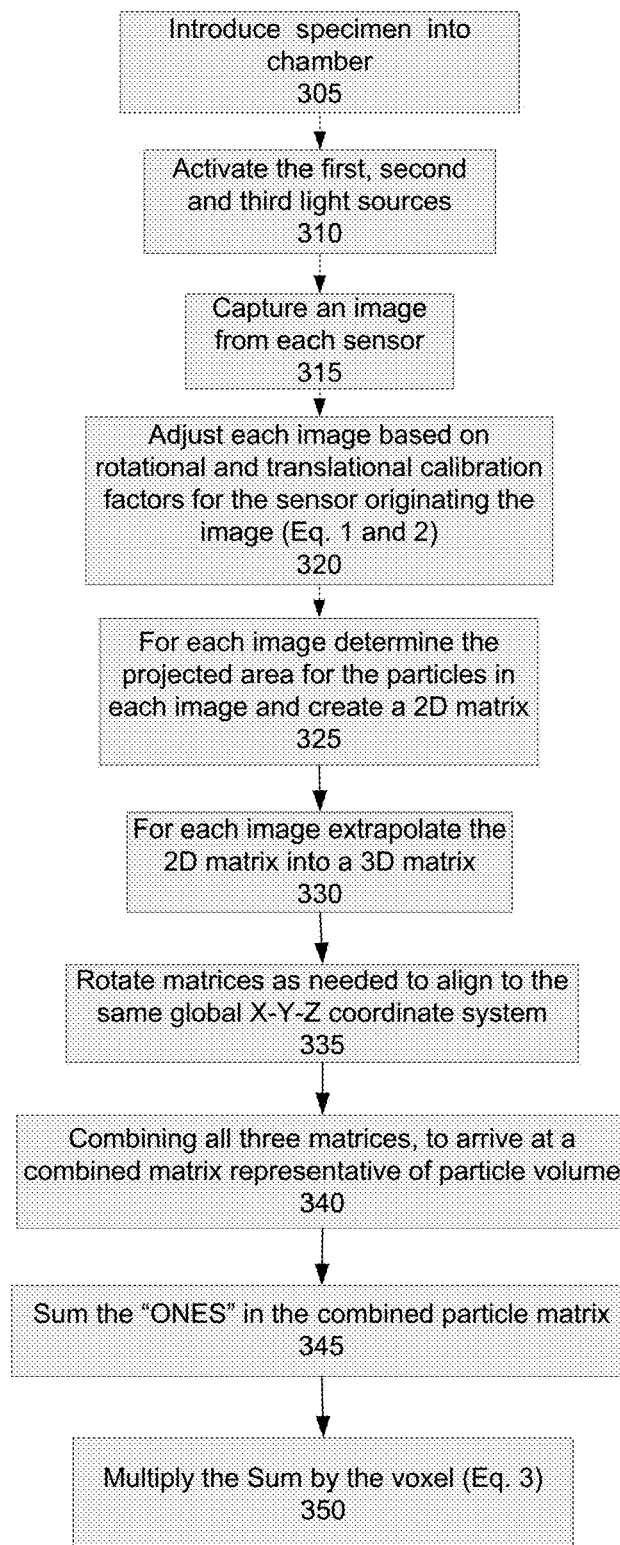
FIG. 12 is a flowchart for a method of calculating the estimated volume of particles within a chamber.

Once the three orthogonal optical assemblies have been calibrated to the same prism, particle samples may be introduced into the system, and the volume of those particles can be estimated using method 300 described in the flowchart presented in FIG. 12. A specimen is introduced into the specimen at step 305, and the three light sources are activated (step 310). An image from each of the three sensors is captured (step 315), and at step 320 each image is adjusted based on the rotational and translational calibration factors for the sensor originating the image (Eq. 1 and 2). For each image from each sensor, determine the projected area for the particles in each image and create a 2D matrix (step 325).

Extrapolate each 2D matrix into a 3D matrix (step 330) and rotate the 3D matrices as necessary to align all the 3D matrices to the same global X-Y-Z coordinate system (step 335). Then at step 340, the three 3D matrices are combined using the logical AND operation, and the combined matrix is summed at step 345. This sum is then multiplied by the voxel (Eq. 3) to determine the actual estimate of particle volume (step 350).

Although exemplary embodiments and applications of the invention have been described herein including as described above and shown in the included examples, there is no intention that the invention be limited to these exemplary embodiments and applications or to the manner in which the exemplary embodiments and applications operate or are described herein. Indeed, many variations and modifications to the exemplary embodiments are possible, as would be apparent to a person of ordinary skill in the art. The invention may include any device, structure, method, or functionality, as long as the resulting device, system or method falls within the scope of one of the claims that are allowed by the patent office based on this or any related patent application.

The invention claimed is:

1. A system for calculating the volume of a plurality of particles moving within a transparent or translucent chamber defining a chamber position, the system comprising:
   three optical assemblies, each comprising:
      a light source directing a beam of light of a wavelength along an optical axis at the chamber position;
      a filter positioned along the optical path after the chamber position, wherein the filter preferentially allows the light emitted from the light source through; and
      a sensor positioned along the optical path after the filter;
   wherein the wavelength of beam of light for each optical assembly is different than the wavelengths of the other optical assemblies;
   wherein the optical axis for each optical assembly is orthogonal to each of the optical axes of the other optical assemblies;
   a three-dimension calibration prism, constructed to be removably placed in the chamber position, the prism comprising a calibration fiducial plane that intersects each of the three optical axes, and wherein, within the calibration fiducial plane, a plurality of calibration fiducials are separated by known distances;
   a processor connected to the sensors in each of the optical assemblies, the processor adapted to perform the following steps:
      a. place the calibration prism at the chamber position;
      b. capture an image from each of the three sensors;
      c. determine calibration factors for each sensor based on the known distances of the calibration fiducials detected in the images;
      d. remove the calibration prism from the chamber position;
      e. introduce a sample to the chamber;
      f. capture an image from each of the three sensors;
      g. calibrate the images based on the calibration factors;
      h. create a two-dimensional matrix based on the projection made by the particles for each image;
      i. extrapolate each two-dimensional matrix into a three-dimensional matrix;
      j. combine all three-dimensional matrices to form a three-dimensional volume matrix; and
      k. calculate a volume based on the sum of the three-dimensional volume matrix and the calibration factors.

2. The system of claim 1, wherein the light sources are a red, green and blue laser.

3. The system of claim 1, wherein the calibration factors include a rotational, a translational and a size calibration factor for each optical assembly.

4. The system of claim 1, wherein the plurality of calibration fiducials comprises a center fiducial that is in the geometric center of the calibration prism and three outer calibration fiducials arranged as follows;
   the distance D1 between each of the outer fiducials is equal; and
   the distance D2 between each of the outer fiducials to the center fiducial is equal.

5. The system of claim 4 wherein D1 is equal to D2.

6. A method of aligning and calibrating a system with three orthogonal optical assemblies, each assembly including a light source directing a light beam at a specimen chamber along an optical axis and a sensor positioned along the optical path to capture images of the specimen chamber, the method comprising the following steps:
   inserting an calibration prism into the system, wherein the calibration prism comprises a calibration fiducial plane that intersects each of the three optical axis, and within the calibration fiducial plane a plurality of calibration fiducials that are separated by known distances;
   activating each of the light sources;
   obtaining an image from each of the sensors;
   detecting the calibration fiducials in each obtained image;
   for each sensor, calculating a rotational calibration factor based on locations of the calibration fiducials in the sensor image;
   for each sensor, calculating a translational calibration factor based on the locations of the calibration fiducials in the sensor image;
   for each sensor, calculating a size calibration factor based on the locations of the calibration fiducials in the sensor image;
   removing the calibration prism from the system;
   capturing an image from each of the three sensors;
   applying the rotational calibration factor and size calibration factor to the images;
   determining a volume of the plurality of particles based on the captured images by the following steps:
      creating a two-dimensional matrix based on the projection made by the particles for each image;
      extrapolating each two-dimensional matrix into a three-dimensional matrix;
      combining all three-dimensional matrices to form a three-dimensional volume matrix; and
   calculating a volume based on the sum of the three-dimensional volume matrix.

7. The method of claim 6, wherein the calculation of the volume is based on the size calibration factors.

8. The method of claim 6, wherein prior to combining the three-dimensional matrices, the two-dimensional matrices are rotated, as needed, to align each of the two-dimensional matrices to the same coordinate system.

* * * * *